United States Patent [19]

Ojima

[11] Patent Number: 6,096,909
[45] Date of Patent: Aug. 1, 2000

[54] TAXOID ANTI-TUMOR AGENTS AND PHARMACEUTICAL COMPOSITIONS THEREOF

[75] Inventor: Iwao Ojima, Stony Brook, N.Y.

[73] Assignee: The Research Foundation of State University of New York, Stony Brook, N.Y.

[21] Appl. No.: 08/910,742

[22] Filed: Aug. 13, 1997

Related U.S. Application Data

[63] Continuation of application No. 08/330,956, Oct. 28, 1994, abandoned.

[51] Int. Cl.[7] .................. C07D 305/14; A61K 31/337
[52] U.S. Cl. .................. 549/510; 549/511; 514/449
[58] Field of Search .................. 549/510, 511; 514/449

[56] References Cited

U.S. PATENT DOCUMENTS

| | | | |
|---|---|---|---|
| 4,960,790 | 10/1990 | Stella et al. | 514/449 |
| 5,059,699 | 10/1991 | Kingston et al. | 549/511 |
| 5,229,526 | 7/1993 | Holton | 549/213 |
| 5,284,864 | 2/1994 | Holton et al. | 514/449 |
| 5,294,737 | 3/1994 | Ojima | 562/444 |
| 5,739,362 | 4/1998 | Holton et al. | 549/510 |

FOREIGN PATENT DOCUMENTS

| | | |
|---|---|---|
| 0558959 | 9/1993 | European Pat. Off. . |
| 0604910 | 7/1994 | European Pat. Off. . |
| 0639577 | 2/1995 | European Pat. Off. . |
| WO94/10996 | 5/1994 | WIPO . |
| WO94/10997 | 5/1994 | WIPO . |
| WO94/17050 | 8/1994 | WIPO . |
| WO94/21250 | 9/1994 | WIPO . |

OTHER PUBLICATIONS

Greene et al, "Protective Group in Organic Synthesis", 2nd ed., 1991, pp. 10–12.

Ojima et al. "Synthesis and Biological Activity of 3'-Alkyl-and 3'-Alkyl-and 3'-Alkenyl-3'-Dephenyldocetaxels", Bioorganic & Medicinal Chemistry Letters, vol. 4, No. 21, pp. 2631-2634 (1994).

Ojima et al., "N-Acyl-3-Hydroxy-β-lactams as Key Intermediates for Taxotere and its Analogs" Bioorganic & Medicinal Chemistry Letters, vol. 3, No. 11, pp.2479–2482, Apr. 1993.

Ojima et al., "A Highly Efficient Route to Taxotere by the β-Lactam Synthon Method"; Tetrahedron Letters, vol. 34, No. 26, pp. 4149–4152, 1993.

Ojima et al., "New and Efficient Routes to Norstatine and its Analogs with High Enantiomeric Purity by β-Lactam Synthon Method"; Tetrahedron Letters, vol. 33, No. 39, pp. 5737–5740, 1992.

Ojima et al., "New and Efficient Approaches to the Semi-synthesis of Taxol and its C–13 Side Chain Analogs by Means of β–Lactam Synthon Method"; Tetrahedron vol. 48, No. 34, pp. 6985–7012, 1992.

Iwao Ojima, "In Vitro Evaluation," Department of Experimental Therapeutics, Roswell Park Cancer Institute, Sheet A, Aug. 26, 1994.

Iwao Ojima, "In Vitro Evaluation," Department of Experimental Therapeutics, Roswell Park Cancer Institute, Sheet B, May 24, 1994.

Iwao Ojima, Olivier Duclos, Scott D. Kuduk, Chung–Ming Sun, John C. Slater, François Lavelle, Jean M. Veith, and Ralph J. Bernacki, "Synthesis and Biological Activity of 3'-Alkyl-and 3'-Alkenyl-3'-Dephenyldocetaxels", Bioorganic & Medicinal Chemistry Letters, vol. 4, No. 21, pp. 2631–2634, Sep. 7, 1994.

Primary Examiner—Ba K. Trinh
Attorney, Agent, or Firm—Finnegan, Henderson, Farabow, Garrett & Dunner, L.L.P.

[57] ABSTRACT

This invention relates to a taxoid of the formula (I)

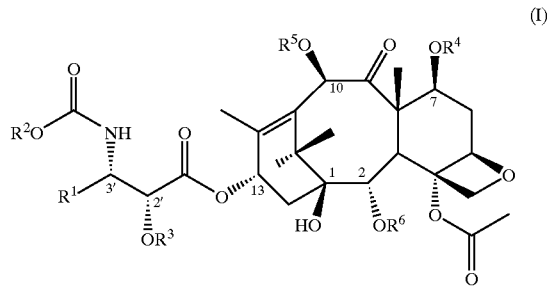

wherein $R^1$ is 1-propenyl radical;

$R^2$ is a $C_3$–$C_5$ branched alkyl radical;

$R^3$ and $R^4$ are independently selected from hydrogen and hydroxyl protecting groups including functional groups which increase the water solubility of the taxoid antitumor agent;

$R^5$ represents a hydrogen or a hydroxyl protecting group;

$R^6$ represents an acyl radical, which are useful as antitumor agents or their precursors. A pharmaceutical composition having antineoplastic activity comprising the compound of formula (I) and a physiologically acceptable carrier and method of treatment are also disclosed.

6 Claims, No Drawings

TAXOID ANTI-TUMOR AGENTS AND PHARMACEUTICAL COMPOSITIONS THEREOF

This is a continuation of application Ser. No. 08/330,956, filed Oct. 28, 1994, now abandoned.

FIELD OF INVENTION

The present invention relates to new taxoids possessing strong antitumor activities, the precursors of these antitumor taxoids, and pharmaceutical compositions thereof.

BACKGROUND OF THE INVENTION

Taxol (paclitaxel), a complex diterpene, is currently considered the most exciting lead in cancer chemotherapy. Paclitaxel possesses high cytotoxicity and strong antitumor activity against different cancers which have not been effectively treated by existing antitumor drugs. For example, paclitaxel has been approved by FDA in late 1992 for the treatment of advanced ovarian cancer and for breast cancer in 1994. Paclitaxel is currently in phase II and III clinical trial for lung cancer and other cancers.

Although paclitaxel is an extremely important "lead " in cancer chemotherapy, it is common that better drugs can be derived from naturally occurring lead compounds. In fact, French researchers have discovered that a modification of the C-13 side chain of paclitaxel brought about a new anticancer agent which seems to have antitumor activity superior to paclitaxel with better bioavailability. This unnatural compound was named "Taxotère (docetaxel)", which has t-butoxycarbonyl instead of benzoyl on the amino group of (2R,3S)-phenylisoserine moiety at the C-13 position and a hydroxyl group instead of acetoxy group at C-10. Docetaxel is currently in phase II and III clinical trials in United States, Europe, and Japan, which have shown excellent activities, especially against breast and lung cancers.

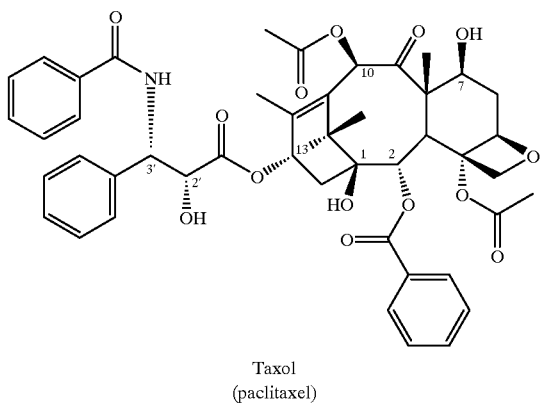

Taxol
(paclitaxel)

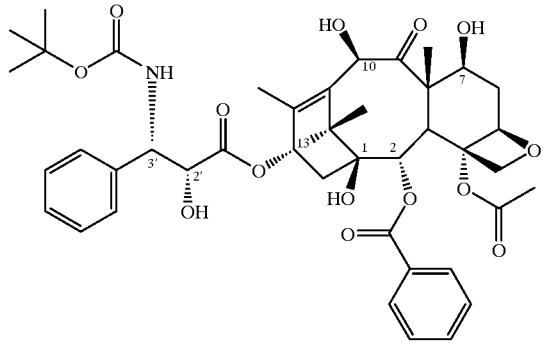

Taxotere
(docetaxel)

A recent report on clinical trials of paclitaxel and docetaxel has disclosed that paclitaxel causes, e.g., nerve damage, muscle pain or disturbances in heart rhythm, whereas docetaxel provokes, e.g., mouth sores and plunge in white blood cells. Other less serious side effects also exist for these two drugs. Therefore, it is very important to develop new anti-cancer drugs which have less undesirable side effects, better pharmacological properties, improved activity against drug-resistant tumors, and/or activity spectra against various tumor types different from those of these two drugs.

It was an objective of the present invention to develop such new anti-tumor agents of paclitaxel class, i.e., taxoids, which have distinct structural differences from those of paclitaxel and docetaxel.

It is the object of the present invention to provide a series of new taxoids bearing 1-propenyl group at the C-3' position instead of a phenyl group, which possess strong antitumor activities with better therapeutic profile, in particular against drug-resistant tumors. One of the serious drawbacks that paclitaxel and docetaxel is the fact that these two drugs pass only a weak activity against drug-resistant tumors, e.g., adriamycin-resistant breast cancer. The new taxoids of the present invention have shown not only stronger antitumor activities against human ovarian, non-small cell lung, colon, and breast cancers than those of the two drugs, but also exhibit more than one order of magnitude better activity against an adriamycin-resistant human breast cancer cells than those of the two drug. Multi-drug-resistance (MDR) is a serious issue in clinical oncology, and thus the new taxoid antitumor agents of this invention will serve as important drugs to overcome this problem.

SUMMARY OF THE INVENTION

A taxoid of the formula (I)

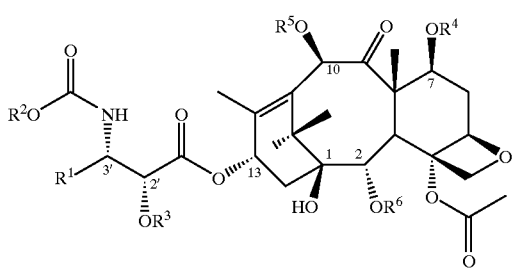

(I)

in which
- $R^1$ is 1-propenyl radical;
- $R^2$ is a $C_3$–$C_5$ branched alkyl radical;
- $R^3$ and $R^4$ are independently selected from hydrogen and hydroxyl protecting groups including functional groups which increase the water solubility of the taxoid antitumor agent;
- $R^5$ represents a hydrogen or a hydroxyl protecting group;
- $R^6$ represents an acyl radical, are useful as antitumor agents or their precursors.

These new taxoids (I) are synthesized by the processes which comprise the coupling reactions of the baccatin of the formula (II)

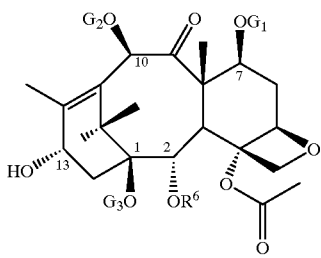

(II)

wherein $G_1$, $G_2$, and $G_3$ represents an hydroxyl protecting group;
$R^6$ has been defined above.
with the B-lactams of the formula (II)

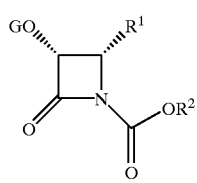

(III)

where in G is a hydroxyl protecting group such as ethoxyethyl (EE), triethylsilyl (TES), (tert.-butyl)dimethylsilyl (TBS), and triisopropylsilyl (TIPS);

$R^1$ and $R^2$ have been defined hereinabove;
in the presence of a base.

DETAILED DESCRIPTION OF THE INVENTION

New taxoids of the formula (I) hereinabove are useful as antitumor agents or their precursors. These taxoids possess strong antitumor activities against, human breast, non-small cell lung, ovarian, and colon cancers including drug-resistant cancer cells as well as leukemia and melanoma.

The new taxoid of the formula (I) are synthesized by modifying the baccatin of the formula (II)

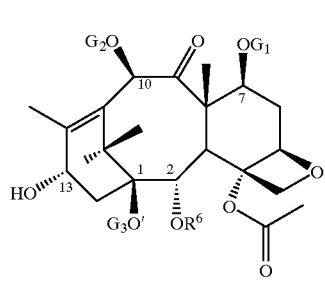

(II)

wherein $G_1$, $G_2$, $G_3$, and $R^6$ have been defined hereinabove.

The baccatin (II) are coupled with the B-lactams of the formula (III)

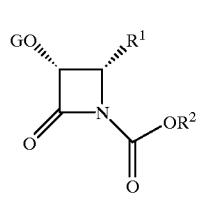

(III)

wherein G, $R^1$ and $R^2$ have been defined hereinabove, to yield the new taxoids (I).

The B-lactams (III) are readily prepared via the B-lactams (IV) which are easily obtained through the chiral enolate—imine cyclocondensation method that has been developed in the present inventors laboratory as shown in Scheme 1 (Ojima et al., Bioorg. Med. Chem. Lett., 1993, 3, 2479. Ojima et al., Tetrahedron Lett., 1993, 34, 4149. Ojima et al., Tetrahedron Lett. 1992, 33, 5739. Ojima et al., Tetrahedron, 1992, 48, 6985; Ojima, I. et al., J. Org. Chem., 1991, 56, 1681). In this preparation, the B-lactams (IV) with extremely high enantiomeric purities are obtained in high yields. In Scheme 1, R* is a chiral auxiliary moiety which is (−)-trans-2-phenyl-1-cyclohexyl or (−)-10-dicyclohexylsulfamoyl-D-isobornyl, TMS is a trimethylsilyl radical, and base is lithium diisopropylamide or lithium hexamethyldisilazide; G and $R^1$ have been defined hereinabove.

Scheme 1

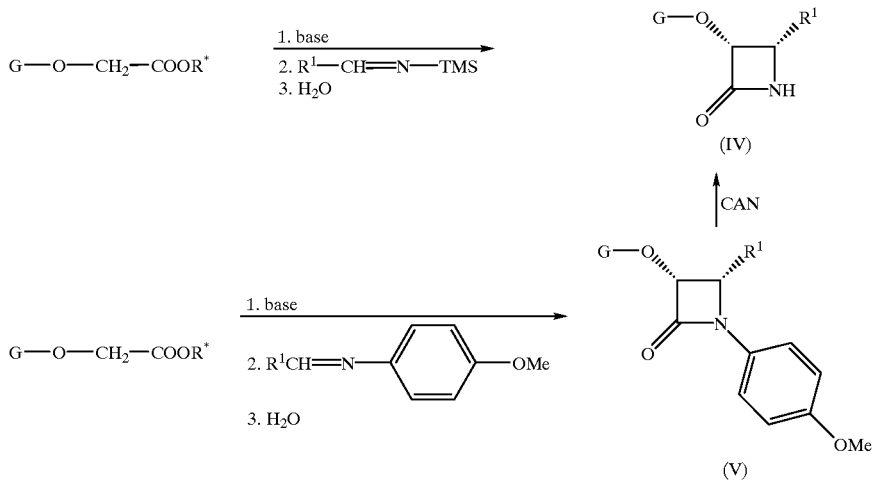

The B-lactams (IV) can be converted to the corresponding N-alkoxycarbonyl-b-lactams (III) in excellent yields by reacting with alkyl chloroformates in the presence of a base (Scheme 2). This transformation is know for those skilled in the art.

The B-lactams (III) are readily used for the coupling with the baccatins (II) in the presence of a base, followed by deprotection to give the new taxoids (I) in high yields $R^1$ through $R^6$ have been defined hereinabove. M is an alkali metal. The hydroxyl protecting groups $G_1$ and $G_2$ are independently selected from methoxylmethyl (MOM), methoxyethyl (MEM), 1-ethoxyethyl (EE), benzyloxymethyl, (b-trimethylsilylethoxyl)methyl, tetrahydropyranyl, 2,2,2-trichloroethoxylcarbonyl (Troc), benzyloxycarbonyl (CBZ), tert-butoxycarbonyl (t-BOC), 9-fluorenylmethoxycarbonyl (Fmoc), 2,2,2-

Scheme 2

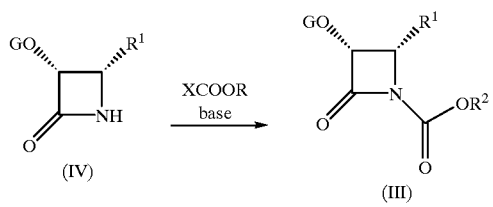

Scheme 3

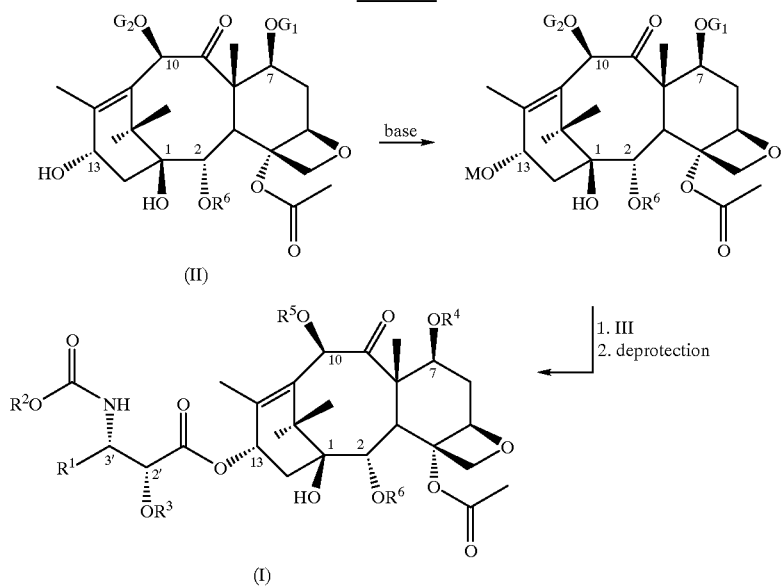

trichloroethoxymethyl, trimethylsilyl, triethylsilyl, tripropylsilyl, dimethylethylsilyl, dimethyl(t-butyl)silyl, diethylmethylsilyl, dimethylphenylsilyl and diphenylmethylsilyl, acetyl, chloroacetyl, dichloroacetyl, trichloroacetyl and trifluoroacetyl.

The coupling reaction of the baccatin (II) and the B-lactam (VI) is carried out via an alkali metal alkoxide of the baccatin (II) at the C-13 hydroxyl group. The alkoxide can readily be generated by reacting the baccatin with an alkali metal base such as sodium hexamethyldisilazide, potassium hexamethyldisilazide, lithium hexamethyldisilazide, sodium diisopropylamide, potassium diisopropylamide, lithium diisopropylamide, sodium hydride, in a dry nonprotic organic solvent such as tetrahydrofuran (THF), dioxane, ether, dimethoxyethane (DME), diglyme, dimethylformamide (DMF), mixtures of these solvents with hexane, toluene, and xylene, in a preferred temperature range from about −100° C. to about 50° C., more preferably at about −78° C. to about 25° C. This reaction is preferably carried out under inert atmosphere such as nitrogen and argon. The amount of the base used for the reaction is preferably approximately equivalent to the amount of the baccatin when soluble bases such as sodium hexamethyldisilazide, potassium hexamethyldisilazide, lithium hexamethyldisilazide, sodium diisopropylamide, potassium diisopropylamide, lithium diisopropylamide are used. The use of a slight excess of the base does not adversely affect the reaction. When heterogeneous bases such as sodium hydride and potassium hydride are used, 5–10 equivalents of the base (to the amount of the baccatin) is preferably employed.

The coupling reaction of the metal alkoxide of the baccatin thus generated with the b-lactam is typically carried out by adding the solution of the B-lactam in a dry organic solvent exemplified above in a preferred temperature range from about −100° C. to 50° C., more preferably at about −35° C. to 25° C. The mixture of reactants is stirred for 15 minutes to 24 hours and the progress and the completion of the reaction is monitored by thin layer chromatography (TLC), for example. When the limiting reactant is completely consumed, the reaction is quenched by addition of a cold brine solution. The crude reaction mixture is worked up using the standard isolation procedures which-are generally known to those skilled in the art to give the corresponding taxoid. The proportion of the b-lactam and the baccatin is in a range from 2:1 to 1:2, more preferably approximately 1:1 for purposes of economy and efficiency, but the ratio is not critical for the reaction.

The hydroxyl protecting groups can then be removed by using the standard procedures which are generally known to those skilled in the art to give the desired taxoid derivatives. For example, EE and TES groups can be removed with 0.5 N HCl at room temperature for 36 h, TIPS and TBS groups can be removed by treating with fluoride ion or HF in a non-protic organic solvent, and Troc group can be removed with zinc and acetic acid in methanol at 60° C. for 1 hour without disturbing the other functional groups and the skeleton of the taxoid.

It has been shown that the introduction of isobutenyl group to the C-3' position of paclitaxel appears to increase the cytotoxicity, especially against drug-resistant cancer cells: Holton and Nadizadeh claimed in their patent [U.S. Pat. No. 5,284,864 (1994)] that 3'-dephenyl-3'-isobutenylpaclitaxel (RAH-1) exhibited 4 times better activity than paclitaxel and 7 times better activity than docetaxel against human colon carcinoma cells HCT-116, and also about 20 times better activity than paclitaxel and 9 times better activity than docetaxel against multi-drug resistant phenotype human colon carcinoma cells HCT-116/VM. We have found that the structural requirements for taxoid antitumor agents to express strong potency are rather strict and unpredictable. For example, 3'-dephenyl-3'-(2-phenylethenyl)docetaxel, bearing 2-phenylethenyl group instead of the isobutenyl group of RAH-1, has dramatically decreased cytotoxicity (>20 times) and 3'-dephenyl-3'-neopentyldocetaxel, bearing neopentyl group which has just one more methyl than isobutenyl group, is virtually not cytotoxic against A121 human ovarian , A549 human non-small cell lung, HT-29 human colon and MCF7 human breast cancer cells. After searching for the best substituent for the C-3' position by employing many alkyl groups and alkenyl groups by tries and errors, we have identified 1-propenyl group to be the optimum substituent, and completed this invention. For example, 3'-dephenyl-3'-(1-propenyl)docetaxel (Taxoid Ia) showed considerably better activity spectrum than that of paclitaxel and docetaxel against human ovarian, human non-small cell lung, human colon, and human breast cancer cells mentioned above (see TABLE 1 in EXAMPLE 8). Moreover, this agent possesses 21 times better activity than paclitaxel and 17 times better activity than docetaxel against the drug-resistant human breast cells MCF7-R, which are mammary carcinoma cells 180 fold resistant to a widely used anticancer drug, adriamycin. In the same assay, Holton's compound RAH-1 showed only marginal activity that was one order of magnitude weaker than that of Taxoid Ia (see TABLE 1 in EXAMPLE 8).

The taxoids of the formula (I) of this invention are useful for inhibiting tumor growth or regression of tumors in animals including humans and are preferably administered in the form of a pharmaceutical composition including effective amounts of the antitumor agent of this invention in combination with a pharmaceutically acceptable vehicle or diluent.

The pharmaceutical compositions of the antitumor agents of the present invention may be made up in any form suitable for desired use, e.g., oral, parenteral or topical administration. Examples of parenteral administration are intramuscular, intravenous, intraperitoneal, rectal, and subcutaneous administration. The vehicle or diluent ingredients should not reduce the therapeutic effects of the antitumor agents of this invention.

Suitable dosage forms for oral use include tablets, dispersible powders, granules, capsules, suspension, syrups, and elixirs. Examples of inert diluents and vehicles for tablets include calcium carbonate, sodium carbonate, lactose and talc. Examples of inert diluents and vehicles for capsules include calcium carbonate, calcium phosphate, and kaolin.

Dosage forms appropriate for parenteral administration include solutions, suspensions, dispersions, and emulsions.

The water solubility of the antitumor agents of the formula (I) may be improved by modifying the C-2' and/or C-7 substituents to incorporate suitable functional groups, $R^3$ and $R^4$. In order to increase the water solubility, $R^3$ and $R^4$ can be independently selected from hydrogen and —CO—X—Y, wherein X is selected from —$(CH_2)_n$—,—(n=1–3), —CH=CH—, cyclohexanediyl, and benzenediyl;

Y is selected from —COOH and its pharmaceutically acceptable salts, —$SO_3H$ and its pharmaceutically acceptable salts, —$NR^7R^8$ and its pharmaceutically acceptable salts, pharmaceutically acceptable ammonium salt —N≈$R^7R^8R^9$, —$CONR^8R^9$, and —$COOR^9$, in which $R^7$ and $R^8$ are independently selected from hydrogen, allyl, $C_1$–$C_6$ alkyl, and $R^9$; —$NR^7R^8$ includes cyclic amine radicals selected from pyrrolidinyl, piperidinyl, morphorino, piperazinyl, and N-methylpiperazinyl;

$R^9$ is selected from $C_1$–$C_6$ alkyl, allyl, —$(CH_2)_n$—Z (n=1–3), wherein Z is selected from —COOH and its pharmaceutically acceptable salts, —$SO_3H$ and its pharmaceutically acceptable salts, —$NR^7R^8$ and its pharmaceutically acceptable salts, pharmaceutically acceptable ammonium salt —$N\approx R^7R^8R^{10}$, in which $R^{10}$ is selected from hydrogen, allyl, and $C_1$–$C_6$ alkyl The preparation of the water-soluble analogs of paclitaxel bearing the functionalized acyl groups described above has been precedented [Kingston et al., U,S, Pat. No. 5,059,699 (1991); Stella et al., U.S. Pat. No. 4,960,790 (1990)] and thus it is not difficult for the people in the skilled art to carry out such modifications.

The following non-limiting examples are illustrative of the present invention. It should be noted that various changes would be made in the above examples and processes therein without departing from the scope of the present invention. For this reason, it is intended that the illustrative embodiments of the present application should be interpreted as being illustrative and not limiting in any sense.

EXAMPLE 1

Preparation of (-)-(1R,2S)-2-phenyl-1-cyclohexyl triisopropylsilyloxyacetate: A solution of (-)-(1R,2S)-2-phenyl-1-cyclohexyl hydroxyacetate (851 mg, 3.63 mmol) was prepared through esterification of benzyloxyacetyl chloride with (-)-(1R,2S)-2-phenyl-1-cyclohexanol followed by hydrogenolysis. Then, triisopropylsilyl chloride (840 mg, 4.36 mmol) and imidazole (618 mg, 9.08 mmol) in dimethylformamide (DMF) (1.7 mL) was stirred at room temperature for 12–20 hours. The mixture was poured into pentane (25 mL), and washed with water and brine. The combined organic layers were dried over anhydrous $MgSO_4$ and concentrated in vacuo. The crude product was subjected to a purification on a short silica gel column using hexane/chloroform (3/1) as the eluant to give pure (-)-(1R,2S)-2-phenyl-1-cyclohexyl triisopropylsilyloxyacetate (1.35 g, 95% yield) as a colorless oil.: $[a]_D^{20}$ –17.1° (c 3.15, CHCl3); IR (neat) 1759, 1730 ("CO) $cm^{-1}$; $^1H$ NMR (CDCl$_3$) d 0.93–0.99 (m, 21H), 1.30–1.62 (m, 4H), 1.72–2^A0 (m, 3H), 2.10–2.19 (m, 1H), 2.66 (dt, J=11.5, 4.0 Hz, 1H), 3.90 (d, J=16.6 Hz, 1H), 4.07 (d, J=16.6Hz, 1H), 5.07 (dt, J =10.6, 4.0 Hz, 1H), 7.16–7.30 (m, 5H). Anal. Calcd for $C_{23}H_{38}O_3Si$: C, 70.72; H, 9.81. Found: C, 70.79; H, 9.85.

EXAMPLE 2

Preparations of N-(4-Methoxyphenyl)-1-butenaldimine: To a solution of 0.360 g. (2.9 mmol) of p-anisidine (recrystallized twice from ethanol) in 12 mL of $CH_2Cl_2$ over anhydrous $Na_2SO_4$ was added 0.24 g (3.5 mmol) of 2-butenal (crotonaldehyde) (distilled immediately prior to use) under nitrogen. After 4 hours, $Na_2SO_4$ was filtered off and the solvent removed under vacuum to give N-(4-methoxyphenyl)-1-butenaldimine in quantitative yield, which was used for the synthesis of b-lactam without further purification.

EXAMPLE 3

(3R,4S)-1-(4-Methoxyphenyl)-3-triisopropylsilyloxy-4-(1-propenyl)azetidin-2-one (Va): To a solution of 0.27 mL (1.9 mmol) of diisopropylamine in 10 mL of THF was added 0.76 mL (1.9 mmol) of 2.5M n-butyllithium in hexanes at –10° C. After stirring for 45 minutes, the solution was cooled to –85° C. A solution of (-)-(1R,2S)-2-phenyl-1-cyclohexyl triisopropylsilyloxy-acetate (0.575 g 1.47 mmol) in 10 mL of THF was added via cannula over a period of 1.5 hours. After stirring for an additional hour, a solution of N-(4-methoxyphenyl)-2-butenaldimine (336 mg, 2.2 mmol) in 10 mL of THF was added via cannula over a period of approximately 1 hour. The mixture was stirred for 2 hours and allowed to warm up to room temperature overnight while stirring. The reaction was then quenched with saturated $NH_4Cl$. The aqueous layer was extracted with ethyl acetate (EtOAc) and the combined organic layers were washed with saturated $NH_4Cl$ solution, and brine, and then dried over $MgSO_4$. After the removal of solvent under vacuum, the crude product was obtained, which was purified by flash chromatography on silica gel (hexane:EtOAc=10:1 to 6:1) to afford pure PMP-B-lactam (399 mg, 70% yield) as a rust-colored oil. The enantiomeric purity of the PMP-B-lactam Va was determined to 97% on the basis of chiral HPLC analysis: $[a]_D$=+33.1° (c 0.27, CHCl$_3$); $^1H$ NMR (CDCl$_3$, 250 MHz) d 1.04–1.16 (m, 21H), 1.76 (dd, J=6.5, 1.3 Hz, 3H), 3.74 (s, 3H), 4.51 (dd, J=8.6, 5.0 Hz, 1H), 5.04 (d, J=5.0 Hz, 1H), 5.59 (ddd, J=15.4, 8.6, 1.3 Hz 1H), 5.92 (dq, J=15.4, 6.5 Hz, 1H), 6.83 (d, J=9.0, 2H), 7.36 (d, J=9.0 Hz, 2H)$^{13}C$ NMR (63 MHz, CDCl$_3$) d 11.89, 17.63, 17.68, 55.38, 61.89, 77.57, 114.18, 118.48, 126.65, 1127.48, 128.34, 128.55, 132.59, 156.03, 165.43.

EXAMPLE 4

(3R,4S)-3-Triisopropylsilyloxy-4-(1-propenyl)azetidin-2-one (IVa): To a solution of 260 mg. (0.67 mmol) of N-PMP-b-lactam Va in 20 ml. of acetonitrile at –10° C., was added dropwise a solution of 1.13 g (2.07 mmol) of cerium ammonium nitrate (CAN) in 25 mL of water. The mixture was allowed to stir for 1 hour and then diluted with 50 mL of water. The aqueous layer was extracted with ethyl acetate (2×35 mL) and the combined organic layers were washed with water, 5% $NaHSO_3$, 5% $Na_2CO_3$, and brine. After drying over $MgSO_4$ and concentrating under vacuum, the organic layers afforded the crude product, which was purified on a silica gel column using hexane-ethyl acetate as the eluant (hexane:EtOAc=3:1) to give the pure b-lactam IVa (124 mg, 65% yield) as a pale yellow viscous oil: $^1H$ NMR (CDCl$_3$, 250 MHz) d 1.04–1.16 (m, 21H), 1.70 (dd, J=6.5, 1.2 Hz, 3H), 4.13 (dd, J=8.7, 4.9, 1H), 4.94 (d, J=4.9 Hz, 1H), 5.51 (ddd, J=14.1, 8.7, 1.2 Hz, 1H), 5.67 (m, 1H), 6.68 (br s, 1H); $^{13}C$ NMR (63 MHz, CDCl$_3$) d 11.80, 17.57, 17.62, 58.14, 79.18, 127.97, 130.64, 170.36.

EXAMPLE 5

(3R,4S)-1-tert-Butoxycarbonyl-3-triisopropylsilyloxy-4-(1-propenyl)azetidin-2-one(IIIa): To a solution of 100 mg (0.35 mmol) of the B-lactam IVa, 0.24 mL (1.75 mmol) of triethylamine, and a catalytic amount of dimethylaminopyridine (DMAP) in 11 mL of $CH_2Cl_2$, was added dropwise at room temperature, 85 mg. (0.38 mmol) of di(tert.-butyl) dicarbonate in 2 mL of $CH_2Cl_2$. The mixture was stirred for 1 hour and quenched with saturated $NH_4Cl$ solution. The mixture was diluted with 60 mL of ethyl acetate and the organic layer was washed with brine, dried over $MgSO_4$, and concentrated. The crude product was purified by flash chromatography on silica gel (hexane:EtOAc=4:1) to yield pure N-[4]BOC-B-lactam IIIa as colorless oil (105 mg, 87% yield): $^1H$ NMR (CDCl$_3$, 250 MHz) d 1.02–1.08 (m, 21H), 1.48 (s, 9H), 1.74 (dd, J=6.4, 1.3 Hz, 3H), 4.44 (dd, J=8.6, 5.8 Hz, 1H), 4.94 (d, J=5.8 Hz, 1H), 5.54 (ddd, J=15.4, 8.6, 1.3 Hz), 5.83 (dq, J=15.4, 6.4 Hz, 1H); $^{13}$C NMR (63 MHz, CDCl$_3$) d 11.76, 17.52, 17.95, 27.97, 61.04, 83.06, 124.80, 132.72, 148.0, 166.07. Anal. Calcd for C$_{20}$H$_{37}$NO$_4$Si: C, 62.62, H, 9.72, N, 3.65. Found: C, 62.62; H, 9.63; N, 3.61.

EXAMPLE 6

7-Triethylsilyl-10-acetyl-2'-triisopropylsilyl-3'-(1-propenyl)docetaxel (Ia-P): To a solution of 68 mg (0.097 mmol) of 7-TES-baccatin and 58 mg (0.15 mmol) of the N-$^t$BOC-B-lactam (VIa) in 4 mL of THF at –30° C. was added 0.12 mL (0.12 mmol) of LiHMDS. The mixture was allowed to warm to –10° C. and stirred for 1 hour and was then quenched with NH$_4$Cl. The aqueous layer was extracted with 75 mL of EtOAc and the combined organics were washed with NH$_4$Cl and brine. The organics were then dried over MgSO$_4$ and concentrated under vacuum. Upon purification by flash column chromatography on silica gel (hexane:EtOAc=4:1), 83 mg (79% yield) of pure protected taxoid Ia-P was collected (90% conversion, 88% conversion yield) as a white solid: Mp. 131.0–132.5 ° C.; $^1$H NMR (CDCl$_3$, 250 MHz) d 0.57 (q, J=7.7 Hz, 6H), 0.92 (t, J =7.7 Hz, 9H), 1.05–1.11 (m, 21H), 1.20 (s, 3H), 1.23 (s, 3H), 1.32 (s, 9H), 1.69 (s, 3H), 1.73 (d, J 6.2 Hz, 3H), 1.76–1.95 (m, 1H), 2.01 (s, 3H), 2.18 (s, 3H), 2.22–2.35 (m, 2H), 2.41 (s, 3H), 2.43–2.60 (m, 1H), 3.83 (d, J=6.8 Hz, 1H), 4.17 (d, J=8.3 Hz, 1H), 4.31 (d, J=8.3 Hz, 1H), 4.42–4.55 (m, 2H), 4.62 (br m, 1H), 4.85–4.98 (m, 2H), 5.46 (dd, J=14.3, 6.2 Hz, 1H), 5.62–5.75 (m, 2H), 6.18 (t, J=9.1 Hz, 1H), 6.47 (s, 1H), 7.49 (t, J=7.2 Hz, 2H), 7.59 (t, J=7.2 Hz, 1H), 8.11 (d, J =7.2 Hz, 2H); $^{13}$C NMR (63 MHz, CDCl$_3$) d 5.29, 6.71, 10.04, 12.50, 14.41, 17.71, 17.94, 20.85, 21.24, 22.75, 26.39, 28.18, 35.36, 37.21, 43.28, 46.73, 55.0, 58.21, 71.23, 72.24, 74.89, 75.06, 78.05, 79.5, 81.12, 84.24, 127.67, 128.64, 129.25, 130.19, 133.40, 133.53, 140.74, 155.0, 167.0, 169.25, 169.89, 171.64, 203.72.

EXAMPLE 7

3'-Dephenyl-3'-(1-propenyl)-10-acetyl-docetaxel (Ia): To a solution of 46 mg. (0.042 mmol) of the protected taxoid Ia-P in 3 mL of 1:1 mixture of acetonitrile and pyridine was added 0.5 mL of HF/pyridine (70:30). The reaction mixture was stirred at 35–40° C. for 2 hours. The reaction was quenched with 2N HCl. The mixture was extracted with EtOAc and the organic layer washed with 2N HCl and brine. After drying over MgSO$_4$, the crude product was purified by flash chromatography on silica gel (hexane:EtOAc=1:2) to yield 24 mg (70% yield) of the pure taxoid Ia as a white solid: Mp. 152.0–155.0 ° C.; [a]$_D$ –86.70 (c, 0.1 5, CHCl$_3$); $^1$H NMR (CDCl$_3$, 250 MHz) d 1.15 (s, 3H), 1.25 (s, 3H), 1.32 (s, 9H), 1.67 (s, 3H), 1.75 (d, J=6.3 Hz, 3H), 1.86 (br s, 4H), 2.23 (s, 3H), 2.30–2.39 (m, 2H), 2.40 (s, 3H), 2.45–2.60 (m, 1H), 3.38 (br s, 1H), 3.81 (d, J=6.9 Hz, 1H), 4.17 (d, J=8.4 Hz, 1H), 4.30–4.33 (m, 2H), 4.42 (dd, J=10.5, 6.9 Hz, 1H), 4.60 (br m, 1H), 4.90–4.98 (m, 2H), 5.53 (dd, J=16.2, 6.3 Hz, 1H), 5.67 (d, J=6.9 Hz, 1H), 5.72–5.82 (m, 1H), 6.21 (t, J=8.8 Hz, 1H), 6.30 (s, 1H), 7.52 (t, J=7.2 Hz, 2H), 7.61 (t, J=7.2 Hz, 1H), 8.11 (d, J=7.1 Hz, 2H); $^{13}$C NMR (63 MHz, CDCl$_3$) d 9.53, 14.95, 17.87, 20.84, 21.82, 22.54, 26.69, 28.18, 35.45, 35.60, 54.90, 58.62, 72.19, 73.12, 74.98, 75.61, 79.03, 79.55, 81.10, 84.41, 127.37, 128.71, 129.1, 130.19, 133.1, 133.68, 142.50, 155.50, 167.20, 170.13, 171.5, 173.40, 203.73. Anal. Calcd. for C$_{42}$H$_{55}$O$_{15}$N: C, 61.98; H, 6.81; N, 1.72. Found: C, 62.12; H, 6.59; N, 1.67.

EXAMPLE 8

Taxoid Ia was evaluated in their tumor growth inhibitory activities against human tumor cell line, A121 (ovarian carcinoma), A549 (non-small cell lung carcinoma), HT-29 (colon carcinoma), MCF7 (mammary carcinoma) or MCF7-R (mammary carcinoma cells 180-fold resistant to adriamycin), after 72 h drug exposure according to the literature method (see below). Results are shown in Table 1. Lower numbers indicate higher potency. Paclitaxel, docetaxel, and RAH-1 (see above) were also used for comparison. The data represent the mean values of at least three separate experiments. Lower numbers indicate greater activity.

TABLE 1

| Taxoid | A121[a] (ovarian) | A549[a] (NSCLC) | HT-29[a] (colon) | MCF7[a] (breast) | MCF7-R[a] |
|---|---|---|---|---|---|
| Paclitaxel | 6.1 | 3.6 | 3.2 | 1.7 | 300 |
| Docetaxel | 1.2 | 1.0 | 1.2 | 1.0 | 235 |
| RAH-1 | 1.4 | 0.45 | 0.96 | 0.54 | 113 |
| Ia | 0.90 | 0.54 | 0.76 | 0.51 | 14 |

[a]The concentration of compound which inhibit 50% (IC$_{50}$, nM) of the growth of human tumor cell line.

Assessment of cell growth inhibition was determined according to the methods of Skehan et al [Skehan et al., J. Nat. Cancer Inst. 1990, 82, 1107.]. Briefly, cells were plated between 400 and 1200 cells/well in 96 well plates and incubated at 37° C. for 15–18 h prior to drug addition to allow attachment of cells. Compounds tested were solubilized in 100% DMSO and further diluted in RPMI-1640 containing 10 mM HEPES. Each cell line was treated with 10 concentrations of compounds (5 log range). After a 72 h incubation, 100 mL of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 mL) was added to each well. Following a 5 min incubation at room temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

Data were fit with the Sigmoid-Emax concentration-effect model [see Holford, N. H. G.; Scheiner, L. B., "Understanding the dose-effect relationship: Clinical applications of pharmaco-kinetic-pharmacodynamic models.", *Clin. Pharmacokin.* 1981, 6, 429–453] with non-linear regression, weighted by the reciprocal of the square of the predicted response. The fitting software was developed by the Roswell Park Cancer Institute with Microsoft FORTRAN, and uses the Marquardt algorithm [see Marquardt, D. W., "An algorithm fir least squares estimation of nonlinear parameters", *J. Soc. Ind. Appl. Math.* 1963, 11, 431–441] as adopted by Nash [see Nash, J. C., "Compact numerical method for computers: Linear algebra and function minimization", John Wiley & Sons, New York, 1979.] for the non-linear regression. The concentration of drug which resulted in 50% growth inhibition (IC$_{50}$) was calculated.

We claim:

1. A taxoid of the formula (I):

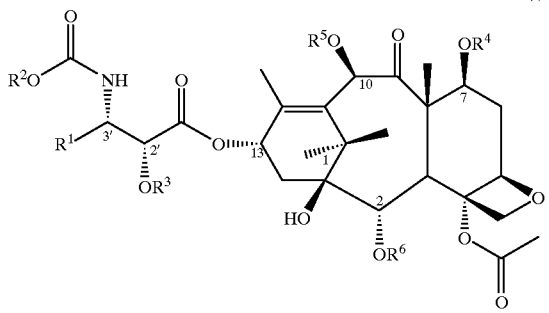

wherein
- $R^1$ is a 1-propenyl radical;
- $R^2$ is a $C_3$—$C_5$ branched alkyl radical;
- $R^3$ and $R^4$ are hydrogen;
- $R^5$ represents an acyl radical other than an acetyl radical, or a benzoyloxycarbonyl or alkoxycarbonyl radical; and
- $R^6$ represents an acyl radical.

2. A taxoid according to the claim 1 wherein $R^2$ is selected from isopropyl, cyclopropyl, isobutyl, sec.-butyl, tert.-butyl, cyclobutyl, 1-ethylpropyl, and 1,1-dimethylpropyl radicals.

3. A taxoid according to the claim 1 wherein

- $R^2$ is a tert.-butyl radical;
- $R^5$ is a benzoyloxycarbonyl radical; and
- $R^6$ is a benzoyl, 3-fluorobenzoyl, 3-azidobenzoyl, or cyclohexane carbonyl radical.

4. A pharmaceutical composition having antineoplastic activity comprising the compound of claim 1 and a physiologically acceptable carrier therefor.

5. A method for treating tumors which comprises administrating to a patient an effective antitumor amount of the compound of claim 1.

6. A method according to claim 5 wherein said treatment comprises treating tumors selected from the group consisting of leukemia, melanoma, breast, non-small cell lung, ovarian, and colon cancers.

* * * * *